(12) United States Patent
Janik et al.

(10) Patent No.: US 6,816,570 B2
(45) Date of Patent: Nov. 9, 2004

(54) MULTI-TECHNIQUE THIN FILM ANALYSIS TOOL

(75) Inventors: Gary R. Janik, Palo Alto, CA (US); Jeffrey Moore, Redwood City, CA (US)

(73) Assignee: KLA-Tencor Corporation, San Jose, CA (US)

( * ) Notice: Subject to any disclaimer, the term of this patent is extended or adjusted under 35 U.S.C. 154(b) by 221 days.

(21) Appl. No.: 10/094,537

(22) Filed: Mar. 7, 2002

(65) Prior Publication Data

US 2003/0169846 A1 Sep. 11, 2003

(51) Int. Cl.$^7$ .............................................. G01B 15/02
(52) U.S. Cl. ........................ 378/50; 378/89; 250/310
(58) Field of Search ...................... 378/50, 89, 98.8, 378/42, 54; 250/310

(56) References Cited

U.S. PATENT DOCUMENTS

| | | | |
|---|---|---|---|
| 5,619,548 A | | 4/1997 | Koppel |
| 5,656,812 A | * | 8/1997 | Takahashi ................ 250/310 |
| 5,877,498 A | * | 3/1999 | Sugimoto et al. ........... 250/310 |
| 6,292,532 B1 | * | 9/2001 | Kawahara et al. ............ 378/49 |

* cited by examiner

Primary Examiner—Craig E. Church
Assistant Examiner—Irakli Kiknadze
(74) Attorney, Agent, or Firm—Bever, Hoffman & Harms, LLP; John M. Kubodera

(57) ABSTRACT

A thin film analysis system includes multi-technique analysis capability. Grazing incidence x-ray reflectometry (GXR) can be combined with x-ray fluorescence (XRF) using wavelength-dispersive x-ray spectrometry (WDX) detectors to obtain accurate thickness measurements with GXR and high-resolution composition measurements with XRF using WDX detectors. A single x-ray beam can simultaneously provide the reflected x-rays for GXR and excite the thin film to generate characteristic x-rays for XRF. XRF can be combined with electron microprobe analysis (EMP), enabling XRF for thicker films while allowing the use of the faster EMP for thinner films. The same x-ray detector(s) can be used for both XRF and EMP to minimize component count. EMP can be combined with GXR to obtain rapid composition analysis and accurate thickness measurements, with the two techniques performed simultaneously to maximize throughput.

70 Claims, 7 Drawing Sheets

MULTI-TECHNIQUE THIN FILM ANALYSIS TOOL

BACKGROUND OF THE INVENTION

1. Field of the Invention

The present invention relates to the area of thin film analysis. In particular, the present invention relates to a method and apparatus for combining multiple thin film analysis capabilities into a single instrument.

2. Discussion of Related Art

As the dimensions of semiconductor devices continue to shrink, accurate and efficient characterization of the components forming those devices becomes more critical. Typically, the manufacturing process for modern semiconductor devices includes the formation of a number of layers or "thin films", such as oxide, nitride, and metal layers. To ensure proper performance of the finished semiconductor devices, the thickness and composition of each film formed during the manufacturing process must be tightly controlled. In the realm of thin film analysis, three basic techniques have evolved to measure film thickness and composition.

Grazing-incidence X-ray Reflectometry

Grazing-incidence x-ray reflectometry (GXR), which is sometimes referred to as x-ray reflectometry (XRR), measures the interference patterns created by reflection of x-rays off a thin film. FIG. 1 shows a conventional x-ray reflectometry system 100, as described in U.S. Pat. No. 5,619,548, issued Apr. 8, 1997 to Koppel. X-ray reflectometry system 100 comprises a microfocus x-ray tube 110, an x-ray reflector 120, and a detector 130. X-ray reflectometry system 100 is configured to analyze a test sample 140 that includes a thin film layer 142 formed on a substrate 141.

Microfocus x-ray tube 110 directs a source x-ray beam 150 at x-ray reflector 120. Source x-ray beam 150 typically comprises a bundle of diverging x-rays that can have a variety of different wavelengths. X-ray reflector 120 reflects and focuses the diverging x-rays of x-ray beam 150 into a converging x-ray beam 160. Typically, x-ray reflector 120 is a singly- or doubly-curved monochromatizing crystal that ensures that only x-rays of a particular wavelength are included in converging x-ray beam 160, which is directed at thin film layer 142.

Converging x-ray beam 160 is then reflected by thin film layer 141 as an output x-ray beam 170 onto detector 130. X-ray beam 170 forms an interference pattern on the surface of detector 130 due to constructive and destructive interference of x-ray reflections at the top and bottom surfaces of thin film layer 142. Detector 130 is a position-sensitive detector that measures the varying intensity of this interference pattern. The resulting reflectivity curve of intensity versus position can then be used to calculate the thickness of thin film layer 142, as described in U.S. Pat. No. 5,619,548.

GXR is best suited for measuring thickness and electron density for films in the range of 10A–2000A thick. It is well matched to the barrier/seed film stacks used in BEOL (back end of line) copper interconnects. However, GXR cannot measure thicker ECP (electrochemical plated) copper films having thicknesses greater than 1 um. Furthermore, GXR is not very good at measuring the composition of thin films—for example the composition of a barrier film such as TaN or TiSiN.

Electron Microprobe Analysis

To analyze the composition of a thin film layer, a technique known as electron microprobe (EMP) analysis is often used. EMP analysis involves the use of an electron beam (e-beam) to generate characteristic x-rays from a thin film layer. FIG. 2 shows a conventional EMP system 200 comprising an e-beam generator 210 and an x-ray detector 230. EMP system 200 is configured to analyze a test sample 240 that includes a thin film layer 242 formed on a substrate 241.

To perform an EMP analysis, e-beam generator 210 directs an e-beam 250 at thin film layer 242. The high-energy electrons in e-beam 250 cause characteristic x-rays 290 to be emitted by thin film layer 242. The properties of characteristic x-rays 290 are then measured by x-ray detector 230 to determine the composition of thin film layer 242.

Generally, x-ray detector 230 comprises either an energy-dispersive x-ray spectrometer (EDX or EDS) or a wavelength-dispersive x-ray spectrometer (WDX or WDS). In an EDX detector, the energies of the characteristic x-rays are used to determine the composition of the thin film.

FIG. 4a shows a conventional EDX detector 230a that includes a detector crystal 231 and a pulse analyzer 232. Each of characteristic x-rays 290 incident on detector crystal 231 deposits an amount of charge proportional to the energy of that particular x-ray. These charge pulses are then measured by pulse analyzer 232. Because different elements generate x-rays having different energies, the charge pulse magnitudes read by pulse analyzer 232 can be used to determine the intensity of the characteristic x-rays, which in turn can be used to determine thin film composition and thickness.

While an EDX detector provides a relatively simple means for determining the composition of a thin film layer, x-rays having closely spaced wavelengths (i.e., energies) can be difficult to distinguish. For example, an ECP copper film may be formed over a tantalum nitride barrier film. The characteristic copper x-rays (Cu-K, indicating x-rays resulting from the ionization of the K shells of the copper atoms) and the characteristic tantalum x-rays (Ta-L, indicating x-rays resulting from the ionization of the L shells of the tantalum atoms) are only separated by 100 eV, and therefore cannot be resolved by an EDX detector, which typically has a resolution limit of greater than 150 eV. Furthermore, an EDX detector cannot detect low energy x-rays, such as those emitted by the nitrogen (N-K x-rays; i.e., x-rays resulting from the ionization of the K shells of the nitrogen atoms) in a barrier film.

In contrast, WDX detectors have a much lower resolution limit of roughly 10–20 eV, and can therefore provide much more accurate measurements than an EDX detector. The low resolution limit of a WDX detector would enable Cu-K and Ta-L x-rays to be distinguished, and also enables the detection of low-energy N-K x-rays. In a WDX detector, x-rays having specific wavelengths are detected to improve the resolution of the measurement process.

FIG. 4b shows a conventional WDX detector 230b that includes an x-ray reflector 238 and a proportional counter 239. Incoming characteristic x-rays 290 are incident on x-ray reflector 238. X-ray reflector 238 is a monochromator, and disperses the incoming characteristic x-rays 290 according to Bragg's Law. X-ray reflector 238 is configured such that only those characteristic x-rays 290 having a specific wavelength are directed onto proportional counter 239. The specific wavelength is selected to be the characteristic wavelength of x-rays emitted by a particular element. Therefore, the output of proportional counter 239 can then be correlated to the concentration of the particular element in the thin film layer. Often, multiple WDX detectors are used simultaneously, with each of the multiple WDX detectors being configured to respond to a different element.

Whether an EDX or WDX detector is used, EMP analysis can be performed relatively quickly due to the intense characteristic x-rays produced by the thin film in response to the e-beam. Also, by varying the energy of the e-beam, an EMP system can "depth profile" a stack of thin film layers, allowing composition measurements to be taken at various positions thoughout the film stack. However, as film thickness in the test sample increases, the electrons in the e-beam must be raised to higher and higher energies to properly penetrate the film. For example, to penetrate 1–2 um thick ECP (electro-chemical plated) copper films, electrons with at least 50 keV energy must be used. Such high-energy electrons are difficult to produce and can damage the test sample. In addition, higher power e-beam generators increase the cost of an EMP system while decreasing overall system reliability. This is in addition to the inherent complexity introduced by vacuum environment required to generate the e-beam.

X-ray Fluorescence

Therefore, for analysis of "thicker" thin films, a technique known as x-ray fluorescence (XRF) is often used. In place of the e-beam used in EMP analysis, XRF analysis uses a source x-ray beam to cause emission of characteristic x-rays from a thin film. The source x-rays can penetrate the film(s) in the test sample much more easily than the electrons used in EMP analysis. For example, the molybdenum x-rays (Mo-K) commonly used in XRF systems can penetrate as much as 20 um of copper, and are therefore much more efficient than an e-beam at measuring thick copper films. FIG. 3 shows a conventional XRF system 300 that includes a microfocus x-ray tube 310, an x-ray reflector 320, and a detector 330. X-ray fluorescence system 300 is configured to analyze a test sample 340 that includes a thin film layer 342 formed on a substrate 341.

Microfocus x-ray tube 310 directs a bundle of diverging x-rays 350 at x-ray reflector 320. X-ray reflector 320 reflects and focuses the diverging x-rays of x-ray beam 350 into a converging x-ray beam 360, directed at thin film layer 342. The x-rays of x-ray beam 360 cause characteristic x-rays 390 to be emitted by thin film layer 342. The properties of characteristic x-rays 390 are then measured by x-ray detector 330 to determine the composition of thin film layer 342, in a manner substantially similar to that used with respect to EMP system 200 shown in FIG. 2. Detector 330 can comprise either an EDX or WDX detector, as described previously with respect to FIGS. 4a and 4b, respectively.

Because x-rays can penetrate a material much more easily than electrons can penetrate the same material, XRF systems are generally better suited to analyze thicker films than are EMP systems. Also, a vacuum chamber is not required for the generation of the source x-rays, which simplifies the design and operation of an XRF system. However, because the source x-rays are not absorbed by the film material as well as electrons would be, and because the source x-ray beam is not as intense as an electron beam can be, the resulting characteristic x-rays in an XRF system are weaker than the characteristic x-rays in an EMP system, making measurements on those characteristic x-rays significantly slower. Also, test samples having multiple thin film layers can be problematic since the source x-rays cannot be readily "tuned" to penetrate to a specific depth Thus, it is clear that no single one of the aforementioned analysis techniques is ideal for all situations. However, having a different set of tools for each set of circumstances can be cumbersome and expensive. This problem can be mitigated somewhat by building multi-technique functionality into a single system. For example, Jordan Valley has produced a tool, the JVX-5000, that combines GXR and XRF capabilities. As noted previously, GXR analysis can be used to measure films less than 2000A thick, while XRF analysis is better suited for thicker films (such as ECP copper layers). However, the Jordan Valley tool incorporates an EDX detector to measure the characteristic x-rays generated during the XRF process, thereby significantly restricting the capabilities of the Jordan Valley tool. As described previously with respect to FIG. 4a, the low resolution of an EDX detector limits its use to materials that generate x-rays having substantially different wavelengths.

Accordingly, it is desirable to provide a tool that includes multi-technique capabilities to overcome limitations associated with individual analysis techniques, while reducing instrument cost, part-count, and increasing analytical efficiency.

SUMMARY

The present invention provides a system and method for incorporating multiple film analysis techniques in a single instrument. This multi-technique capability can enable a user to perform a larger variety of analyses without purchasing multiple tools. Furthermore, combining the components required for the various analytical techniques in a single tool can lead to design and/or usage efficiencies that can reduce costs and increase throughput relative to separate single-technique tools.

According to an embodiment of the present invention, a film analysis system includes both EMP and XRF analysis capabilities. EMP capability is provided by an e-beam generator for directing an e-beam at a sample coating (i.e., a film or films to be analyzed) and an x-ray detector(s) for measuring characteristic x-rays generated by the sample coating in response to the source e-beam. The x-ray detector (s) can be either an EDX detector(s), a WDX detector(s), or a combination of both types. XRF capability is provided by a microfocus x-ray tube and an x-ray beam focusing system for focusing a source x-ray beam from the microfocus x-ray tube onto the sample coating to generate characteristic x-rays via x-ray fluorescence. These characteristic x-rays can be measured by the same x-ray detector(s) used in the EMP analysis, thereby reducing part count and cost of the film analysis system. Furthermore, the film analysis system beneficially enables rapid EMP analysis for thinner films, while providing the capability for performing XRF analysis for thicker films.

According to another embodiment of the present invention, a film analysis system includes both GXR and XRF analysis capabilities. GXR capability is provided by a microfocus x-ray tube, a x-ray beam focusing system for focusing the source x-ray beam from the microfocus x-ray tube onto a sample coating (i.e., a film or films to be analyzed), and a position-sensitive detector for measuring the interference pattern generated by the reflected x-rays from the sample coating. The film analysis system also includes a WDX x-ray detector(s) that can perform XRF analysis on the characteristic x-rays emitted by the sample coating in response the portion of the source x-ray beam that is absorbed, rather than reflected, by the sample coating. Because a separate microfocus x-ray tube and x-ray beam focusing system are not required for the XRF analysis, part count and cost of the film analysis system is reduced. Alternatively, a separate microfocus x-ray tube and x-ray beam focusing system for XRF analysis could be included so that operational settings could be optimized for both the GXR and XRF analyses. In either case, combining the two techniques in a single tool advantageously enables accurate GXR thickness measurement coupled with accurate XRF composition measurement. In addition, the film analysis system beneficially enables the GXR and XRF analyses to be performed simultaneously or in rapid succession with each other, thereby improving analysis throughput. Furthermore, by using a WDX detector(s), the resolution of the XRF analysis is significantly enhanced over conventional tools using an EDX detector(s).

According to another embodiment of the present invention, a film analysis system includes both GXR and EMP analysis capabilities. GXR capability is provided by a microfocus x-ray tube, a x-ray beam focusing system for focusing the source x-ray beam from the microfocus x-ray tube onto a sample coating (i.e., a film or films to be analyzed), and a position-sensitive detector for measuring the interference pattern generated by the reflected x-rays from the sample coating. EMP capability is provided by an e-beam generator for directing an e-beam at the sample coating, and an x-ray detector(s) for measuring characteristic x-rays generated by the sample coating in response to the source e-beam. The x-ray detector(s) can be either an EDX detector(s), a WDX detector(s), or a combination of both types. By combining the two techniques in a single tool, accurate GXR thickness measurement can be coupled with accurate XRF composition measurement. In addition, the film analysis system beneficially enables the GXR and EMP analyses to be performed simultaneously or in rapid succession, thereby improving analysis throughput.

According to another embodiment of the present invention, a film analysis system includes GXR, XRF, and EMP analysis capabilities. GXR capability is provided by a microfocus x-ray tube, a x-ray beam focusing system for focusing the source x-ray beam from the microfocus x-ray tube onto a sample coating (i.e., a film or films to be analyzed), and a position-sensitive detector for measuring the interference pattern generated by the reflected x-rays from the sample coating. EMP capability is provided by an e-beam generator for directing an e-beam at the sample coating, and an x-ray detector(s) for measuring characteristic x-rays generated by the sample coating in response to the source e-beam. The x-ray detector(s) can be either an EDX or WDX detector(s). To minimize component count, XRF capability can be provided by properly selecting and configuring the microfocus x-ray tube, so that a portion of the source x-ray beam is absorbed by the sample coating. The characteristic x-rays emitted by the sample coating in response to the absorbed source x-rays can then be measured by the x-ray detector(s) (used also in for EMP analysis).

Alternatively, to optimize XRF and GXR performance, a second microfocus x-ray tube can be included to generate the source x-ray beam for XRF analyses. In any case, combining all three techniques in a single tool provides maximum flexibility in film analysis, and allows for component count reduction and/or throughput enhancement, as described with respect to the aforementioned embodiments.

The present invention will be more fully understood in view of the following description and drawings.

DETAILED DESCRIPTION

By combining the capability to perform multiple analysis techniques in a single instrument, the present invention advantageously improves overall tool expenses and/or improves analysis throughput.

Electron Microprobe Analysis and X-ray Fluorescence

Figure 5:
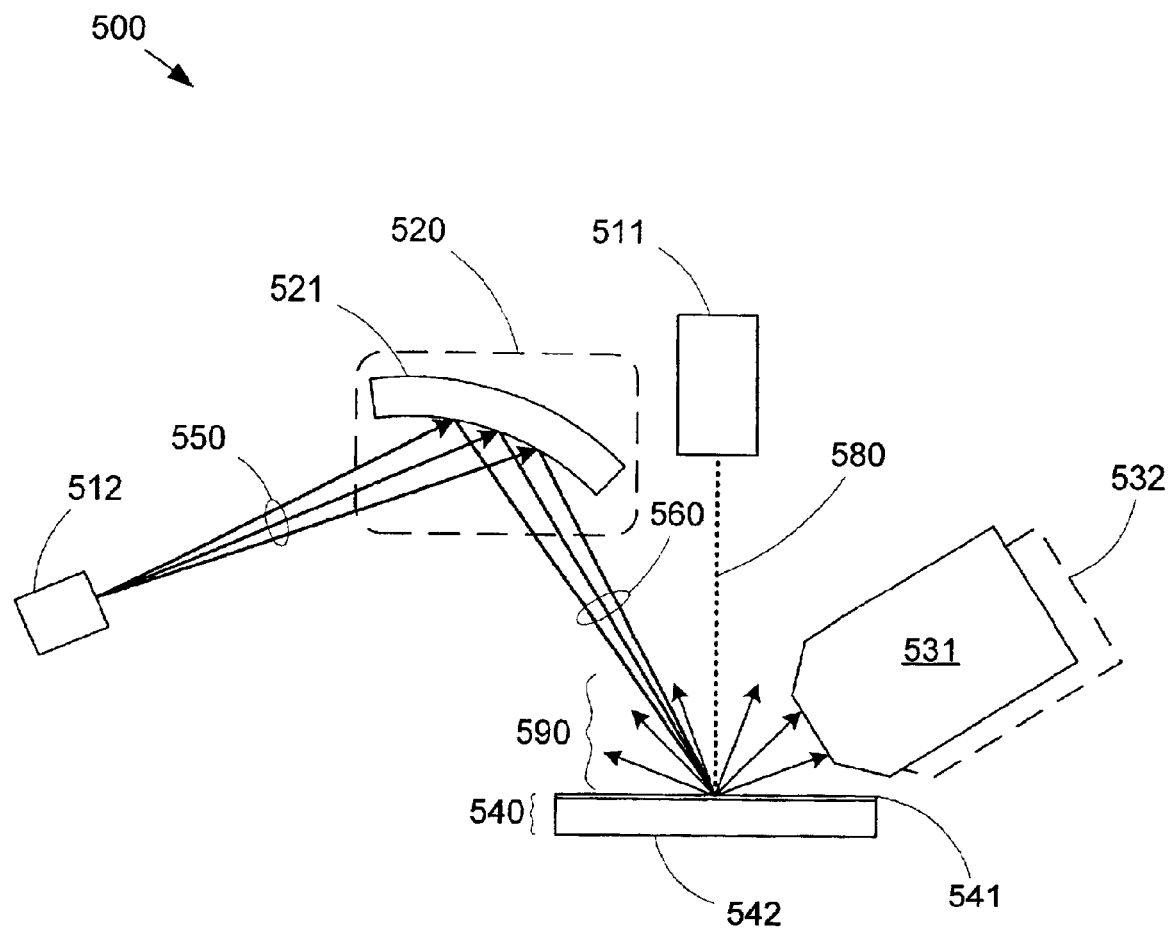
FIG. 5 shows a film analysis system combining XRF and EMP, in accordance with an embodiment of the present invention.

An embodiment of the present invention provides a film analysis system that advantageously combines the rapid measurement capabilities of EMP for thinner films with the thicker film measurement capabilities of XRF. In accordance with an embodiment of the present invention, FIG. 5 shows a film analysis system 500 that comprises a microfocus x-ray tube 512, an x-ray beam focusing system 520, an e-beam generator 511, and an x-ray detector 531. Film analysis system is configured to analyze a test sample 540 that includes a sample coating 541 formed on a substrate 542. Note that substrate 542 can comprise any material on which a coating can be formed, including silicon, gallium arsenide, and metal. Note also that sample coating 541 can comprise any material or materials that can be analyzed using EMP and/or XRF, including oxides, nitrides, copper, titanium, and tantalum, among others. Sample coating 541 can also comprise multiple layers or thin films, such as a copper layer formed over a titanium nitride or tantalum nitride layer.

Figure 4A:
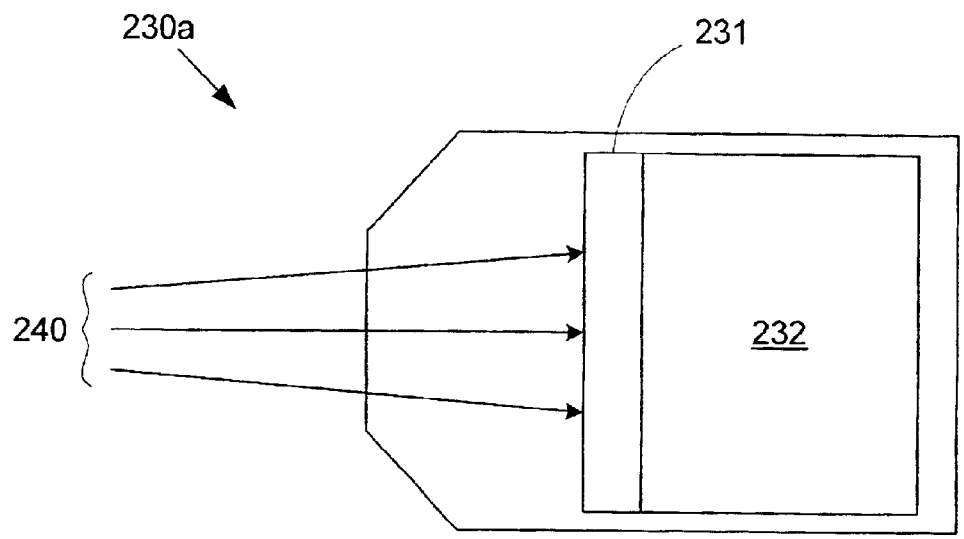
FIG. 4a shows a conventional energy-dispersive x-ray spectrometer (ESX).
Figure 4B:
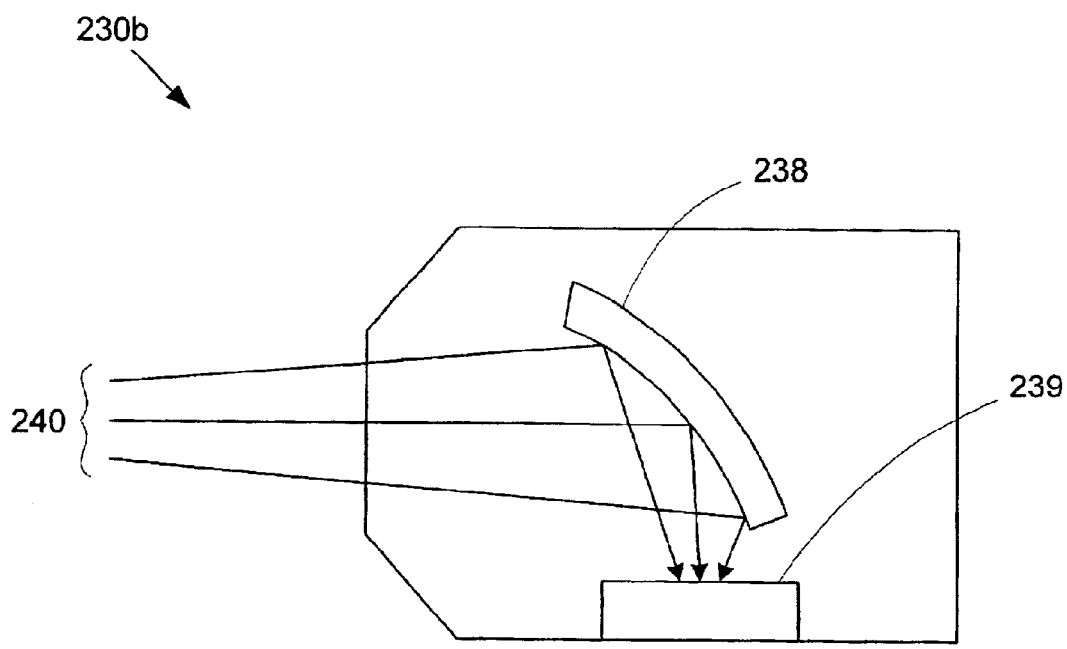
FIG. 4b shows a conventional wavelength-dispersive x-ray spectrometer (WDX).

To perform an EMP analysis, e-beam generator 511 directs an e-beam 580 at sample coating 541. The high-energy electrons in e-beam 580 cause characteristic x-rays 590 to be emitted by sample coating 541. Characteristic x-rays 590 are then measured by x-ray detector 531 to determine the composition and thickness of sample coating 541. According to an embodiment of the present invention, x-ray detector 531 can comprise an EDX detector, as described with respect to FIG. 4a. According to another embodiment of the present invention, x-ray detector 531 can comprise a WDX detector, as described with respect to FIG. 4b, which would improve measurement resolution. Also, film analysis system 500 can comprise multiple x-ray detectors, as indicated by optional x-ray detector 532. While only a single additional x-ray detector (532) is depicted for clarity, film analysis system 500 could comprise any number of x-ray detectors. Multiple WDX detectors would enable simultaneous measurement of characteristic x-rays having different wavelengths (i.e., characteristic x-rays from different elements in sample coating 541).

To perform an XRF operation, microfocus x-ray tube 512 directs an x-ray beam 550 at x-ray beam focusing system 520. X-ray beam focusing system 520 focuses the diverging x-rays of x-ray beam 550 into a converging x-ray beam 560, directed at sample coating 541 of test sample 540. According to an embodiment of the present invention, x-ray beam focusing system 520 can comprise an x-ray reflector 521 that redirects and focuses x-ray beam 550 into x-ray beam 560. X-ray reflector 521 could be a singly- or doubly-curved crystal, and could also be a monochromator to ensure that only x-rays of a particular wavelength are included in x-ray beam 560. However, note that x-ray reflector 521 is depicted for explanatory purposes only, as x-ray beam focusing system 520 can comprise any system for focusing x-ray beam 550 onto sample coating 541. For example, according to another embodiment of the present invention, x-ray beam focusing system 520 can comprise a polycapillary array, in which multiple tubular waveguides direct the incoming x-rays in x-ray beam 550 to a localized spot on sample coating 541.

The x-rays in x-ray beam 560 cause characteristic x-rays 590 to be emitted by sample coating 541. X-ray detector 531 then measures characteristic x-rays 590 to determine the composition and thickness of sample coating 541, in a manner similar to that described with respect to the EMP analysis. If film analysis system 500 includes additional x-ray detectors such as x-ray detector 532, measurements using those additional detectors could be taken at the same time. Because the XRF operation can use at least some of the same x-ray detector(s) as the EMP operation, the cost and complexity of film analysis system 500 is reduced.

The inclusion of both e-beam generator 511 and microfocus x-ray tube 512 greatly increases the flexibility of film analysis system 500 over conventional single-technique tools. For example, a semiconductor manufacturing process might include first process step comprising the formation of a copper (Cu) seed/tantalum nitride (TaN) barrier film stack on a silicon X wafer, followed by a second process step comprising electro-plating a thick copper layer over the Cu—TaN seed/barrier film stack. After the first process step, film analysis system 500 could be used to perform an EMP analysis on the thin films making if up the Cu—TaN seed/barrier stack. Then after the second process step, film analysis system 500 could be used to perform an XRF analysis on the thick ECP copper layer.

Figure 6:
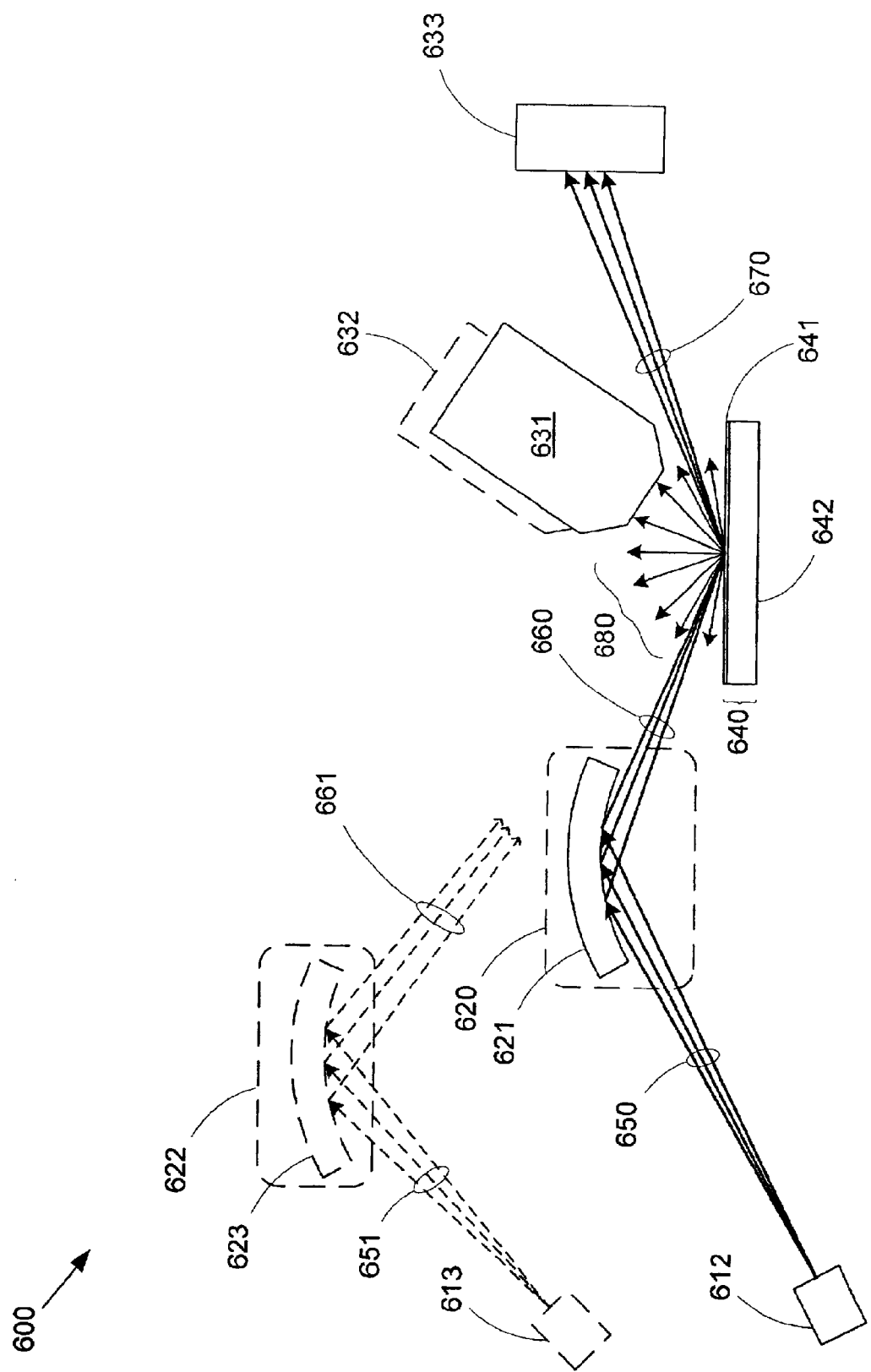
FIG. 6 shows a film analysis system combining GXR and XRF using WDX, in accordance with an embodiment of the present invention.

According to an embodiment of the present invention, e-beam generator 511 could be a variable-power device capable of producing an e-beam 580 having a 5 keV–35 keV energy level, while microfocus x-ray tube 512 could be configured to generate molybdenum x-rays (Mo-K). During the EMP analysis, the Cu-K, Ta-L, and N-K characteristic x-ray intensities could be measured at e-beam energies of 10 keV, 15 keV, and 25 keV to determine the copper seed film and tantalum nitride barrier film thicknesses, along with the tantalum-to-nitrogen ratio in the TaN barrier film. Note that simultaneously measuring all three types of x-rays would require three different x-ray detectors. Note further that, as mentioned previously, WDX detectors would have to be used to differentiate the Cu-K and Ta-L x-rays, as well as detect the softer N-K x-rays. Then during the XRF analysis, the Cu-K and Ta-L x-rays generated in response to the Mo-K x-rays from microfocus x-ray tube 512 could be measured to determine the total thickness of the ECP copper layer and the copper seed film. Note that a similar analytical procedure could be applied to a sample coating that included a titanium nitride barrier film instead of tantalum nitride Grazing Incidence X-ray Reflectometry and X-ray Fluorescence In accordance with an embodiment of the present invention, FIG. 6 shows a film analysis system 600 that advantageously combines the precision thin film thickness measurement capabilities of GXR with the high-resolution composition measurement capabilities of XRF using WDX detectors. Film analysis system 600 comprises a microfocus x-ray tube 612, an x-ray beam focusing system 620, a WDX x-ray detector 631, and a position-sensitive detector 633.

Film analysis system 600 is configured to analyze a test sample 640 that includes a sample coating 641 formed on a substrate 642. As noted previously, substrate 642 can comprise any material on which a film can be formed, while sample coating 641 can comprise a single or multiple films of various compositions.

To perform a GXR analysis, microfocus x-ray tube 612 directs a source x-ray beam 650 at x-ray beam focusing system 620, which reflects and focuses the diverging x-rays of x-ray beam 650 into a converging x-ray beam 660 directed at sample coating 641. According to an embodiment of the present invention, x-ray beam focusing system 620 can comprise an x-ray reflector 621 that redirects x-ray beam 650 into converging x-ray beam 660, focused on a spot on the surface of sample coating 641. X-ray reflector 621 could be a singly- or doubly-curved crystal, and could also be a monochromator to ensure that only x-rays of a particular wavelength are included in x-ray beam 660. However, note that x-ray reflector 621 is depicted for explanatory purposes only, as x-ray beam focusing system 620 can comprise any system for focusing x-ray beam 650 onto sample coating 641. For example, x-ray beam focusing system 620 could comprise a polycapillary array.

Figure 1:
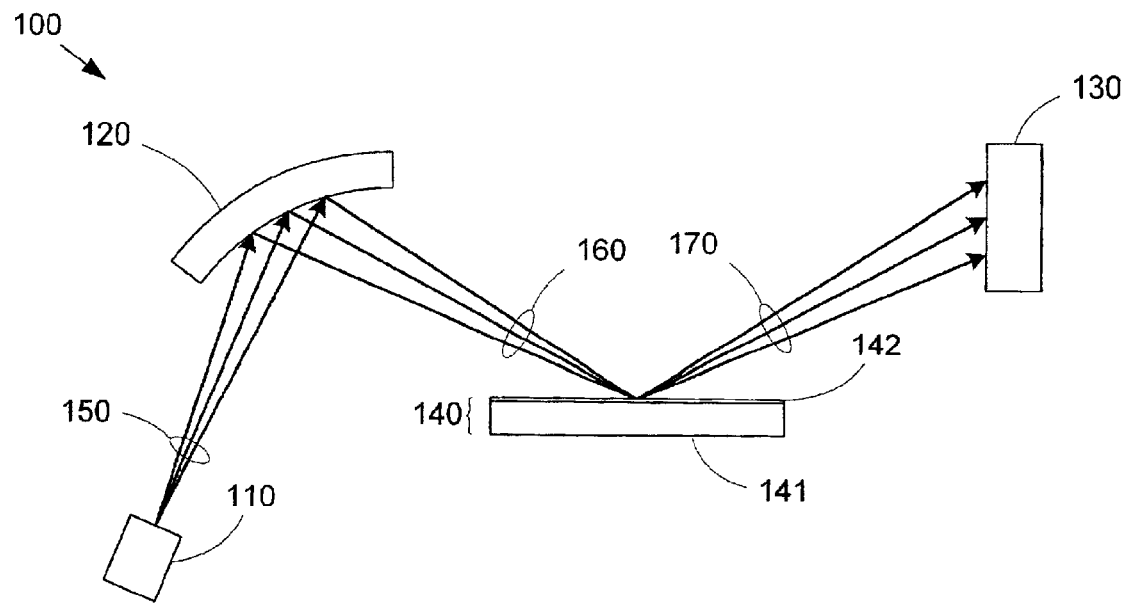
FIG. 1 shows a conventional grazing incidence x-ray reflectometry (GXR) system.
Figure 2:
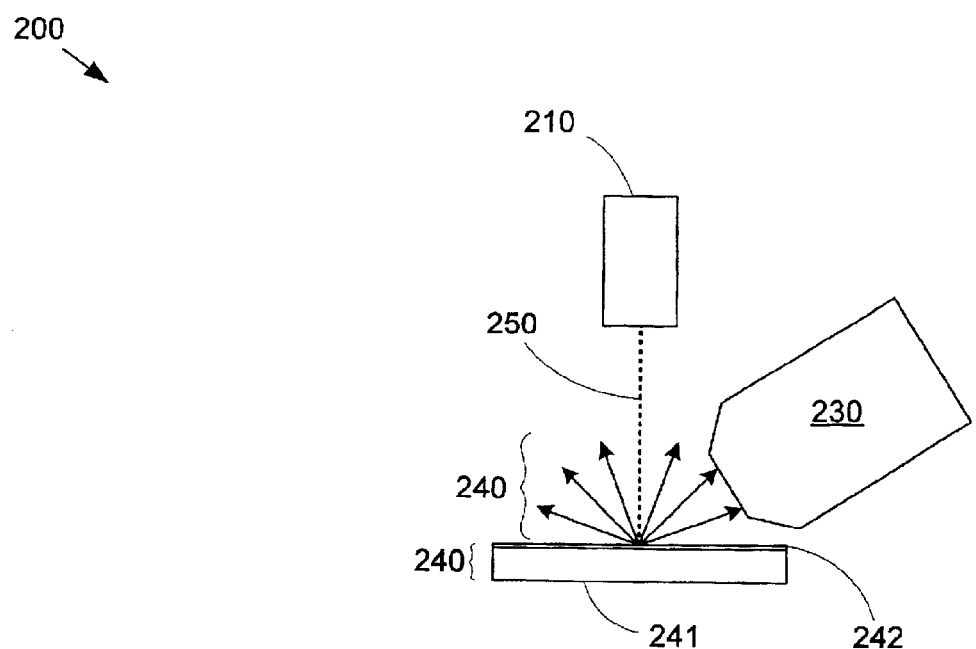
FIG. 2 shows a conventional electron microprobe analysis (EMP) system.
Figure 3:
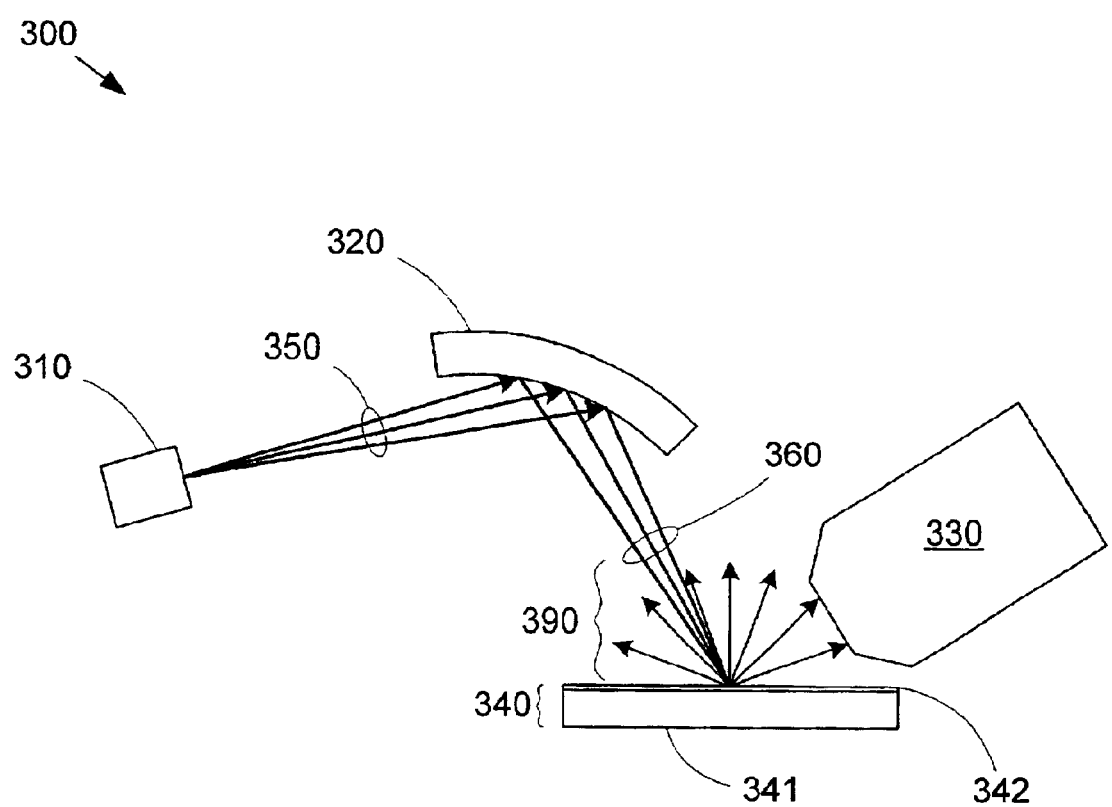
FIG. 3 shows a conventional x-ray fluorescence (XRF) system.

Converging x-ray beam 660 is then reflected by sample coating 641 as an x-ray beam 670 onto position-sensitive detector 633. Position-sensitive detector 633 resolves the varying intensity of the interference pattern caused by constructive and destructive interference of x-ray reflections at the top and bottom surfaces of sample coating 641. The resulting reflectivity curve of intensity versus position can then be used to calculate the thickness of sample coating 641, as described previously with respect to FIG. 1.

Film analysis system 600 can also perform an XRF analysis by making use of the fact that x-ray beam 660 is typically not totally reflected by sample coating 641. During the GXR process, a portion of x-ray beam 660 is absorbed by sample coating 641, rather than being reflected. Note that this proportion of absorbed x-rays can be adjusted by properly selecting and configuring microfocus x-ray tube 612 and x-ray focusing system 620. The absorbed x-rays excite the atoms of sample coating 641, causing them to generate characteristic x-rays 680. Characteristic x-rays 680 can then be measured by x-ray detector 631 to determine the composition of sample coating 641. Note that film analysis system 600 can comprise multiple WDX x-ray detectors, as indicated by optional WDX x-ray detector 632. While only a single additional WDX x-ray detector (632) is depicted for clarity, film analysis system 600 could comprise any number of additional WDX x-ray detectors and/or an EDX detector. Multiple WDX detectors would enable simultaneous measurement of characteristic x-rays having different wavelengths (i.e., characteristic x-rays from different elements in sample coating 641).

By combining GXR and XRF capabilities in film analysis system 600, the thickness of sample coating 641 can be accurately measured using GXR while the composition of sample coating 641 can be accurately determined using XRF. Furthermore, the use of WDX x-ray detector(s) 631 (and 632) enables film analysis system 600 to measure low-energy characteristic x-rays (e.g., N-K x-rays) and closely spaced x-rays (e.g., Cu-K and Ta-L x-rays) that cannot be resolved by the ESX detectors used in conventional tools combining GXR and XRF. For example, sample coating 641 could comprise a copper seed film formed over a tantalum nitride barrier film. According to an embodiment of the present invention, microfocus x-ray tube 612 could be configured to generate high-energy molybdenum x-rays (Mo-K) used to perform a GXR analysis on the copper seed film. At the same time, the Mo-K x-rays would be inducing Cu-K, Ta-L, and N-K characteristic x-rays from the seed/barrier stack, allowing an XRF analysis to be performed on the tantalum nitride barrier film. Because microfocus x-ray tube 612 generates high-energy Mo-K x-rays, a thick ECP copper layer subsequently formed over the copper seed film could be measured by film analysis system 600 using XRF.

According to another embodiment of the present invention, microfocus x-ray tube 612 could be configured to generate lower-energy tungsten x-rays (W-L), in which case simultaneous GXR and XRF analyses could be performed on the seed/barrier stack. A thick ECP copper film could no longer be readily measured by such a system, and a smaller proportion of the low-energy W-L x-rays would be absorbed by sample coating 641, resulting in a reduction in the strength of characteristic x-rays 680. However, this reduced absorption also means a stronger reflected signal, thereby enhancing the GXR fidelity of film analysis system 600. Note that according to another embodiment of the present invention, microfocus x-ray tube 612 could be configured to generate low-energy copper Cu-K x-rays to provide similar measurement capabilities.

In accordance with another embodiment of the present invention, separate x-ray microfocus tubes could be incorporated into film analysis system 600, as indicated by optional microfocus tube 613. One microfocus x-ray tube could then provide the (lower-energy) x-rays for the GXR analysis, while the other could provide the (higher-energy) x-rays for the XRF analysis. For example, microfocus x-ray tube 613 could be configured to provide high-energy Mo-K x-rays for XRF, directing an x-ray beam 651 at an x-ray beam focusing system 622, which focuses a reflected x-ray beam 661 onto sample coating 641. As previously described with respect to x-ray beam focusing system 620, x-ray beam focusing system 622 can comprise any type of beam-guiding system, including an x-ray reflector 623 as depicted, or a polycapillary array (not shown). The high-energy Mo-K x-rays can then cause sample coating 641 to emit strong characteristic x-rays 680, optimizing the associated XRF analysis. Meanwhile, microfocus x-ray tube 612 could be configured to provide lower-energy W-L (or Cu-K) x-rays for the GXR analysis, maximizing the strength of the interference pattern provided at position-sensitive detector 633.

Grazing Incidence X-ray Reflectometry and Electron Microprobe Analysis

Figure 7:
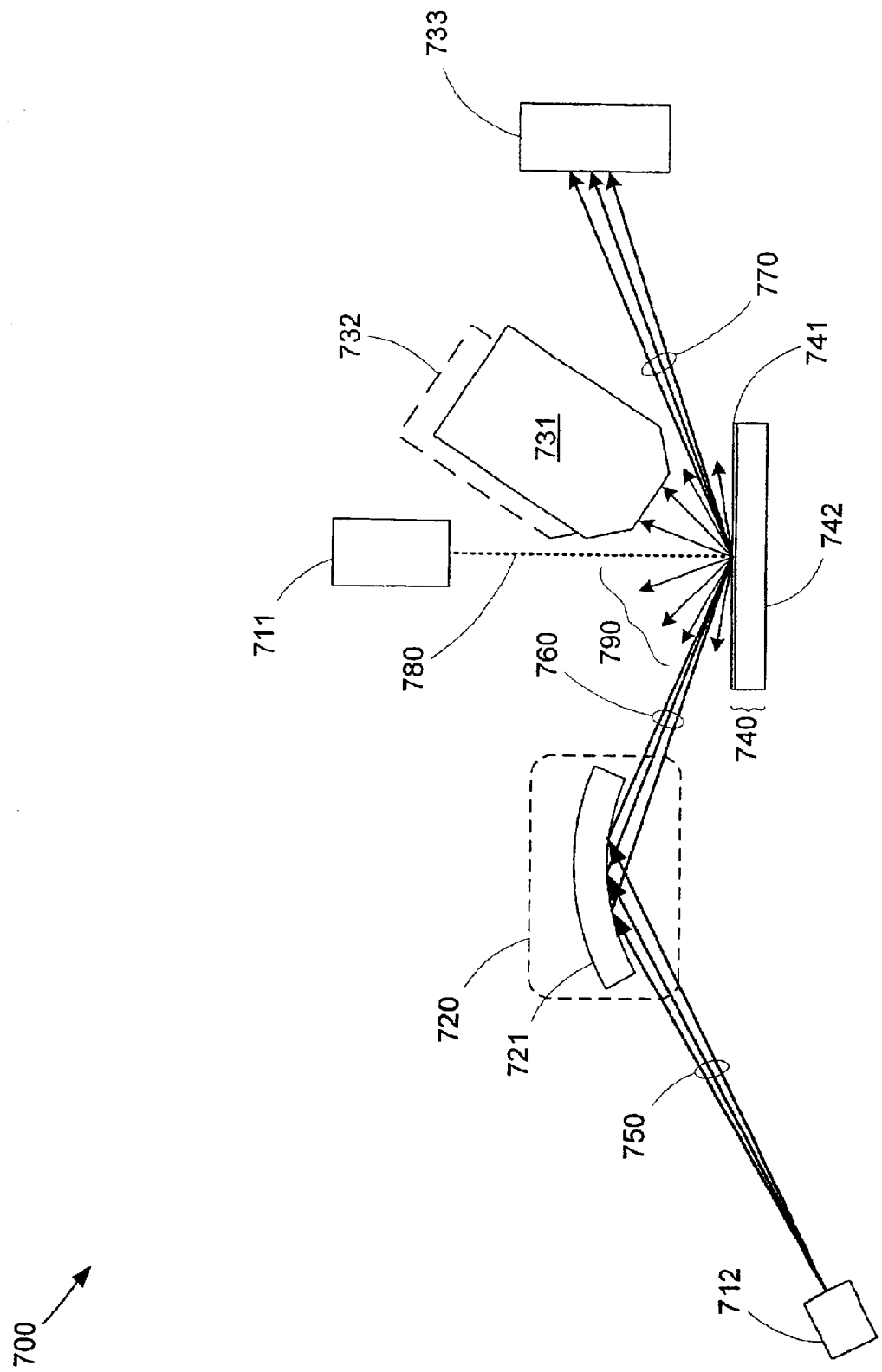
FIG. 7 shows a film analysis system combining GXR and EMP, in accordance with an embodiment of the present invention.

In accordance with an embodiment of the present invention, FIG. 7 shows a film analysis system 700 that combines GXR and EMP capabilities in a single tool, advantageously combining the precision thin film thickness measurement capabilities of GXR with the composition measurement capabilities of EMP. Film analysis system 700 comprises a microfocus x-ray tube 712, an x-ray beam focusing system 720, a position-sensitive detector 733, an e-beam generator 711, and an x-ray detector 731. Film analysis system 700 is configured to analyze a test sample 740 that includes a sample coating 741 formed on a substrate 742. As noted previously, substrate 742 can comprise any material on which a film can be formed, while sample coating 741 can comprise a single or multiple films of various compositions.

To perform a GXR analysis, microfocus x-ray tube 712 directs a source x-ray beam 750 at x-ray beam focusing system 720, which reflects and focuses the diverging x-rays of x-ray beam 750 into a converging x-ray beam 760 directed at sample coating 741. According to an embodiment of the present invention, x-ray beam focusing system 720 can comprise an x-ray reflector 721 that redirects x-ray beam 750 into converging x-ray beam 760, focused on a spot on the surface of sample coating 741. X-ray reflector 721 could be a singly- or doubly-curved crystal, and could also be a monochromator to ensure that only x-rays of a particular wavelength are included in x-ray beam 760. However, note that x-ray reflector 721 is depicted for explanatory purposes only, as x-ray beam focusing system 720 can comprise any system for focusing x-ray beam 750 onto sample coating 741. For example, by configuring microfocus x-ray tube 712 with an additional non-focusing monochromator to produce an x-ray beam 750 made up of x-rays of a single wavelength, monochromatizing by x-ray beam focusing system 720 would not be required, and x-ray beam focusing system 720 could comprise a polycapillary array.

Converging x-ray beam 760 is then reflected by sample coating 741 as an x-ray beam 770 onto position-sensitive detector 733. Position-sensitive detector 733 resolves the varying intensity of the interference pattern caused by constructive and destructive interference of x-ray reflections at the top and bottom surfaces of sample coating 741. The resulting reflectivity curve of intensity versus position can then be used to calculate the thickness of sample coating 741, as described previously with respect to FIG. 1.

To perform an EMP analysis, e-beam generator 711 directs an e-beam 780 at sample coating 741. The high energy electrons in e-beam 780 cause characteristic x-rays 790 to be emitted by sample coating 741. Characteristic x-rays 790 are then measured by x-ray detector 731 to determine the composition and thickness of sample coating 741. According to an embodiment of the present invention, x-ray detector 731 can comprise an EDX detector, as described with respect to FIG. 4a. According to another embodiment of the present invention, x-ray detector 731 can comprise a WDX detector, as described with respect to FIG. 4b, which would improve measurement resolution. Also, film analysis system 700 can comprise multiple x-ray detectors, as indicated by optional x-ray detector 732. While only a single additional x-ray detector (732) is depicted for clarity, film analysis system 700 could comprise any number of additional EDX and/or WDX x-ray detectors. Multiple WDX detectors would enable simultaneous measurement of characteristic x-rays having different wavelengths (i.e., characteristic x-rays from different elements in sample coating 741).

By combining GXR and EMP capabilities in film analysis system 700, the relative weaknesses of each technique can be compensated for by the other. As noted previously, GXR analysis typically does not provide good composition measurement, while EMP typically cannot accurately measure the thickness of a film. However, in film analysis system 700, the thickness of sample coating 741 can be accurately measured using GXR while the composition of sample coating 741 can be accurately determined using EMP. Furthermore, both types of analysis can be performed simultaneously or in rapid succession with each other, significantly improving analysis throughput over conventional systems in which the GXR analysis would be performed in one tool, and the EMP analysis would have to be performed in a different tool, after completion of the GXR analysis.

Figure 8:
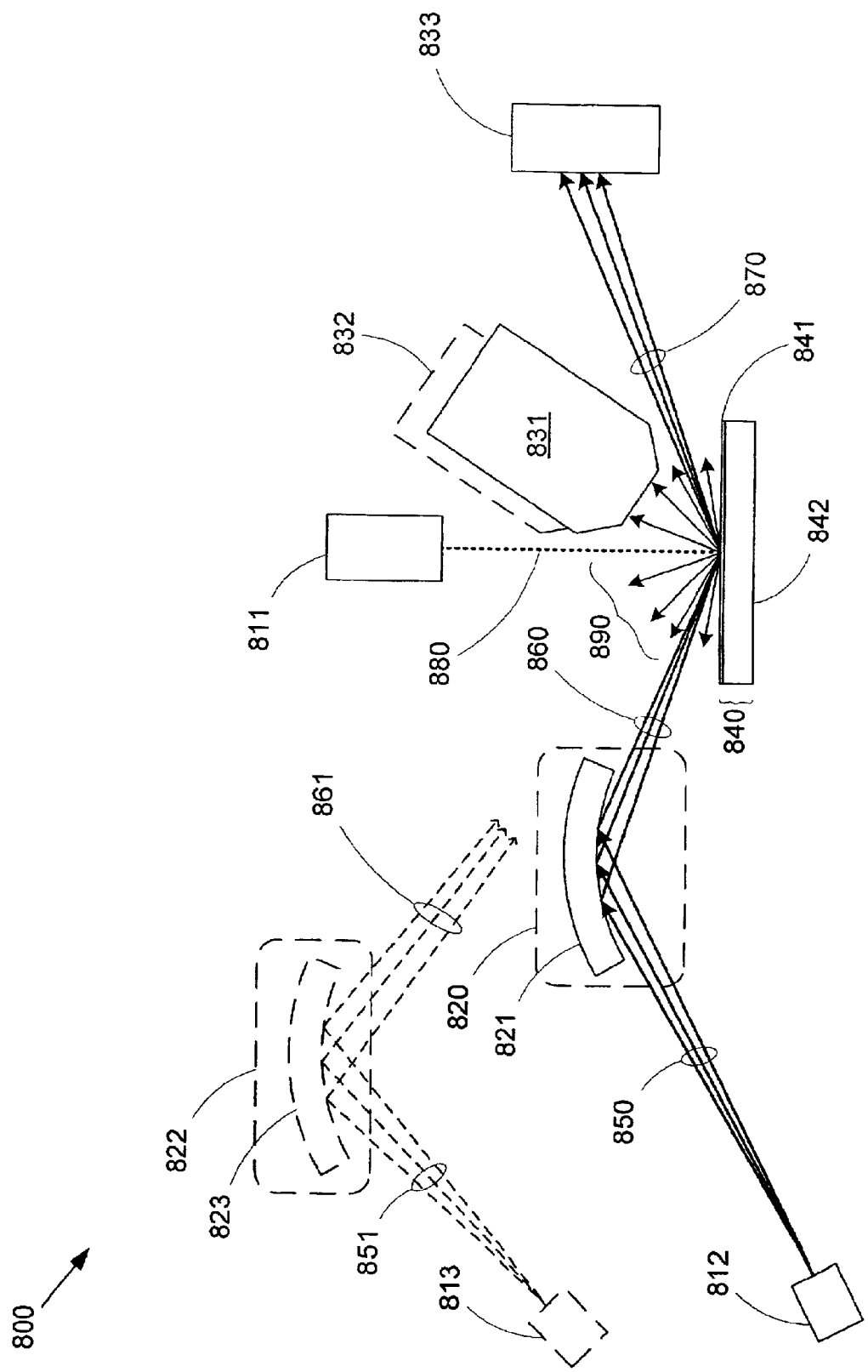
FIG. 8 shows a film analysis system combining GXR, EMP, and XRF, in accordance with an embodiment of the present invention.

Grazing Incidence X-ray Reflectometry, Electron Microprobe Analysis, and X-ray Fluorescence In accordance with an embodiment of the present invention, FIG. 8 shows a film analysis system 800 that advantageously combines the precision film thickness measurement capabilities of GXR with the efficient thin film composition measurement capabilities of EMP and the thicker film composition measurement capabilities of XRF. Film analysis system 800 comprises a microfocus x-ray tube 812, an x-ray beam focusing system 820, an e-beam generator 811, an x-ray detector 831, and a position-sensitive detector 833. Film analysis system 800 is configured to analyze a test sample 840 that includes a sample coating 841 formed on a substrate 842. As noted previously, substrate 842 can comprise any material on which a film can be formed, while sample coating 841 can comprise a single or multiple films of various compositions.

To perform a GXR analysis, microfocus x-ray tube 812 directs a source x-ray beam 850 at x-ray beam focusing system 820, which reflects and focuses the diverging x-rays of x-ray beam 850 into a converging x-ray beam 860 directed at sample coating 841. According to an embodiment of the present invention, x-ray beam focusing system 820 can comprise an x-ray reflector 821 that redirects x-ray beam 850 into converging x-ray beam 860, focused on a spot on the surface of sample coating 841. X-ray reflector 821 could be a singly- or doubly-curved crystal, and could also be a monochromator to ensure that only x-rays of a particular wavelength are included in x-ray beam 860. However, note that x-ray reflector 821 is depicted for explanatory purposes only, as x-ray beam focusing system 820 can comprise any go system for focusing x-ray beam 850 onto sample coating 841. For example, by configuring microfocus x-ray tube 812 with an additional monochromator to produce an x-ray beam 850 made up of x-rays of a single wavelength, monochromatizing by x-ray beam focusing system 820 would not be required, and x-ray beam focusing system 820 could comprise a polycapillary array.

Converging x-ray beam 860 is then reflected by sample coating 841 as an x-ray beam 870 onto position-sensitive detector 833. Position-sensitive detector 833 measures the varying intensity of the interference pattern caused by constructive and destructive interference of x-ray reflections at the top and bottom surfaces of sample coating 841. The resulting reflectivity curve of intensity versus position can then be used to calculate the thickness of sample coating 841, as described previously with respect to FIG. 1.

As described previously with respect to FIG. 6, film analysis system 800 can also perform an XRF analysis by measuring characteristic x-rays 890 generated by those x-rays in x-ray beam 860 that are absorbed by sample coating 842, rather than being reflected. Characteristic x-rays 890 can be measured by x-ray detector 831 to determine the composition of sample coating 841. According to an embodiment of the present invention, x-ray detector 831 can comprise an EDX detector, as described with respect to FIG. 4a. According to another embodiment of the present invention, x-ray detector 831 can comprise a WDX detector, as described with respect to FIG. 4b, which would improve measurement resolution. Also, film analysis system 800 can comprise multiple x-ray detectors, as indicated by optional x-ray detector 832. While only a single additional x-ray detector (832) is depicted for clarity, film analysis system 800 could comprise any number of x-ray detectors. For example, multiple WDX detectors would enable simultaneous measurement of characteristic x-rays having different wavelengths (i.e., characteristic x-rays from different elements in sample coating 841).

In accordance with another embodiment of the present invention, a separate x-ray microfocus tube 813 could provide the excitation source for the XRF analysis. Microfocus x-ray tube 813 would then direct an x-ray beam 851 at an x-ray beam focusing system 822, which would focus a reflected x-ray beam 861 onto sample coating 841. As previously described with respect to x-ray beam focusing system 820, x-ray beam focusing system 822 could comprise any type of beam-guiding system, including an x-ray reflector 823 as depicted, or a polycapillary array (not shown). X-ray detector(s) 831 (and 832) would then measure characteristic x-rays 890 generated by sample coating 841 in response to x-ray beam 861.

Regardless of whether or not film analysis system 800 includes a separate x-ray microfocus tube for XRF analysis, at least some of the same x-ray detector(s) used in the XRF operation can also be used to perform an EMP analysis, by measuring characteristic x-rays 890 generated in response to an e-beam 880 from e-beam generator 811. As previously described with respect to FIG. 5, by sharing some of the same x-ray detectors for both XRF and EMP, the benefits of both analysis techniques can be provided with a minimum of cost and a minimum of equipment. By using the same microfocus x-ray tube 812 for GXR and XRF, the cost and complexity of film analysis system 800 is further reduced, even as the overall capabilities of film analysis system 800 are increased.

Thus, a multi-technique film analysis system is described. Although the present invention has been described in connection with several embodiments, it is understood that this invention is not limited to the embodiments disclosed, but is capable of various modifications that would be apparent to one of ordinary skill in the art. Thus, the invention is limited only by the following claims.

What is claimed is:

1. A thin film analysis system for analyzing a sample coating, the thin film analysis system comprising:

a microfocus x-ray tube for generating a source x-ray beam;

an x-ray beam focusing system for focusing the source x-ray beam onto the sample coating to cause the sample coating to emit a first set of characteristic x-rays;

an electron beam (e-beam) generator for directing an e-beam at the sample coating to cause the sample coating to emit a second set of characteristic x-rays; and a first x-ray detector for measuring a first portion of the first set of characteristic x-rays and a first portion of the second set of characteristic x-rays.

2. The thin film analysis system of claim 1, wherein the x-ray beam focusing system comprises an x-ray reflector.

3. The thin film analysis system of claim 2, wherein the x-ray reflector comprises a doubly curved crystal.

4. The thin film analysis system of claim 2, wherein the x-ray reflector comprises a monochromator.

5. The thin film analysis system of claim 1, wherein the x-ray beam focusing system comprises a polycapillary array.

6. The thin film analysis system of claim 1, wherein the first x-ray detector comprises an energy-dispersive x-ray spectrometer.

7. The thin film analysis system of claim 1, wherein the first x-ray detector comprises a wavelength-dispersive x-ray spectrometer.

8. The thin film analysis system of claim 1, further comprising a second x-ray detector, the second x-ray detector being configured to measure a second portion of the first set of characteristic x-rays and a second portion of the second set of characteristic x-rays, wherein each of the first portion of the first set of characteristic x-rays has a first wavelength, wherein each of the second portion of the first set of characteristic x-rays has a second wavelength, and wherein the first wavelength is different from the second wavelength, and wherein each of the first portion of the second set of characteristic x-rays has a third wavelength, wherein each of the second portion of the second set of characteristic x-rays has a fourth wavelength, and wherein the third wavelength is different from the fourth wavelength.

9. The thin film analysis system of claim 8, wherein the first x-ray detector and the second x-ray detector comprise wavelength-dispersive spectrometers, the first x-ray detector being configured to measure copper Cu-K x-rays, and the second x-ray detector being configured to measure tantalum Ta-L x-rays.

10. The thin film analysis system of claim 8, wherein the first x-ray detector and the second x-ray detector comprise wavelength-dispersive spectrometers, the first x-ray detector being configured to measure copper Cu-K x-rays, and the second x-ray detector being configured to measure titanium Ti-K x-rays.

11. The thin film analysis system of claim 1, the e-beam generator being able to set the e-beam energy between 5 keV and 35 keV.

12. The thin film analysis system of claim 1, the microfocus x-ray tube being configured to generate molybdenum Mo-K x-rays.

13. The thin film analysis system of claim 1, wherein the first x-ray detector comprises a wavelength-dispersive spectrometer, the first x-ray detector being configured to measure nitrogen-N K x-rays.

14. A thin film analysis system for analyzing a sample coating, the thin film analysis system comprising:
 a first microfocus x-ray tube for generating a first source x-ray beam;
 a position-sensitive detector;
 a first x-ray beam focusing system for focusing the first source x-ray beam onto the sample coating, the first source x-ray beam being configured such that a first portion of the first source x-ray beam is reflected onto the position-sensitive detector by the sample coating;
 an electron beam (e-beam) generator for directing an e-beam at the sample coating to cause the sample coating to emit a first set of characteristic x-rays; and
 a first x-ray detector, the first x-ray detector being configured to measure a first portion of the first set of characteristic x-rays.

15. The thin film analysis system of claim 14, wherein the first x-ray beam focusing system comprises an x-ray reflector.

16. The thin film analysis system of claim 15, wherein the x-ray reflector comprises a doubly curved crystal.

17. The thin film analysis system of claim 15, wherein the x-ray reflector comprises a monochromator.

18. The thin film analysis system of claim 14, wherein the first source x-ray beam consists of x-rays having the same wavelength, and wherein the first x-ray beam focusing system comprises a polycapillary array.

19. The thin film analysis system of claim 14, wherein the first x-ray detector comprises an energy-dispersive x-ray spectrometer.

20. The thin film analysis system of claim 14, wherein the first x-ray detector comprises a wavelength-dispersive x-ray spectrometer.

21. The thin film analysis system of claim 14, further comprising a second x-ray detector, the second x-ray detector being configured to measure a second portion of the set of characteristic x-rays, each of the first portion of the first set of characteristic x-rays having a first wavelength, and each of the second portion of the first set of characteristic x-rays having a second wavelength, the first wavelength being different from the second wavelength.

22. The thin film analysis system of claim 21, wherein the first x-ray detector and the second x-ray detector comprise wavelength-dispersive spectrometers, the first x-ray detector being configured to measure copper Cu-K x-rays, and the second x-ray detector being configured to measure tantalum Ta-L x-rays.

23. The thin film analysis system of claim 21, wherein the first x-ray detector and the second x-ray detector comprise wavelength-dispersive spectrometers, the first x-ray detector being configured to measure copper Cu-K x-rays, and the second x-ray detector being configured to measure titanium Ti-K x-rays.

24. The thin film analysis system of claim 14, the e-beam generator being able to set the e-beam energy between 5 KeV and 35 KeV.

25. The thin film analysis system of claim 14, wherein the first x-ray detector comprises a wavelength-dispersive spectrometer, the first x-ray detector being configured to measure nitrogen N-K x-rays.

26. The thin film analysis system of claim 14, wherein the microfocus x-ray tube, the position-sensitive detector, the e-beam generator, and the first x-ray detector can operate simultaneously.

27. The thin film analysis system of claim 14, wherein a measurement of the first portion of the first source x-ray beam by the position-sensitive detector and a measurement of the first portion of the first set of characteristic x-rays by the first x-ray detector can be performed in rapid succession with each other.

28. The thin film analysis system of claim 14, the first source x-ray beam being further configured such that a second portion of the first source x-ray beam is absorbed by the sample coating to cause the sample coating to emit a second set of characteristic x-rays, the first x-ray detector being configured to measure a first portion of the second set of characteristic x-rays.

29. The thin film analysis system of claim 28, wherein the x-ray beam focusing system comprises an x-ray reflector.

30. The thin film analysis system of claim 29, wherein the x-ray reflector comprises a doubly curved crystal.

31. The thin film analysis system of claim 29, wherein the x-ray reflector comprises a monochromator.

32. The thin film analysis system of claim 28, wherein the first source x-ray beam consists of x-rays having the same wavelength, and wherein the first x-ray beam focusing system comprises a polycapillary array.

33. The thin film analysis system of claim 28, wherein the first x-ray detector comprises an energy-dispersive x-ray spectrometer.

34. The thin film analysis system of claim 28, wherein the first x-ray detector comprises a wavelength-dispersive x-ray spectrometer.

35. The thin film analysis system of claim 28, further comprising a second x-ray detector, the second x-ray detector being configured to measure a second portion of the first set of characteristic x-rays and a second portion of the second set of characteristic x-rays,
 each of the first portion of the first set of characteristic x-rays having a first wavelength, and each of the second portion of the first set of characteristic x-rays having a second wavelength, the first wavelength being different from the second wavelength, and each of the first portion of the second set of characteristic x-rays having a third wavelength, and each of the second portion of the second set of characteristic x-rays having a fourth wavelength, the third wavelength being different from the fourth wavelength.

36. The thin film analysis system of claim 28, the first x-ray detector being configured to measure the first portion of the second set of characteristic x-rays at the same time that the position-sensitive detector measures an interference pattern formed by the first portion of the first source x-ray beam after being reflected by the sample coating.

37. The thin film analysis system of claim 28, wherein a measurement of the first portion of the first source x-ray beam by the position-sensitive detector, a measurement of the first portion of the first set of characteristic x-rays by the first x-ray detector, and a measurement of the first portion of the second set of characteristic x-rays by the first x-ray detector can be performed in rapid succession with one another.

38. The thin film analysis system of claim 28, further comprising:
  a second microfocus x-ray tube for generating a second source x-ray beam; and
  a second x-ray beam focusing system for focusing the second source x-ray beam onto the sample coating, the second source x-ray beam onto the sample coating, the second source x-ray beam being configured such that a first portion of the second source x-ray beam is absorbed by the sample coating to cause the sample coating to emit a second set of characteristic x-rays, the first x-ray detector being configured to measure a first portion of the second set of characteristic x-rays.

39. A method for analyzing sample coatings, the method comprising:
  focusing a source x-ray beam onto a first coating of a sample to cause the first coating, to emit a first set of characteristic x-rays;
  measuring a first portion of the first set of characteristic x-rays using a first x-ray detector;
  directing an electron beam (e-beam) at a second coating of the same sample to cause the second coating, to emit a second set of characteristic x-rays; and
  measuring a first portion of the second set of characteristic x-rays using the first x-ray detector.

40. The method of claim 39, wherein the first x-ray detector comprises an energy-dispersive x-ray spectrometer.

41. The method of claim 39, wherein the first x-ray detector comprises a wavelength-dispersive x-ray spectrometer.

42. The method of claim 39, further comprising:
  measuring a second portion of the first set of characteristic x-rays using a second x-ray detector, wherein each of the first portion of the first set of characteristic x-rays has a first wavelength, wherein each of the second portion of the first set of characteristic x-rays has a second wavelength, and wherein the first wavelength is different from the second wavelength; and
  measuring a second portion of the second set of characteristic x-rays using the second x-ray detector, wherein each of the first portion of the second set of characteristic x-rays has a third wavelength, wherein each of the second portion of the second set of characteristic x-rays has a fourth wavelength, and wherein the third wavelength is different from the fourth wavelength.

43. A thin film analysis system for analyzing a sample coating, the thin film analysis system comprising:
  means for generating a source x-ray beam;
  means for focusing the source x-ray beam onto the sample coating to cause the sample coating to emit a first set of characteristic x-rays;
  means for directing an electron beam (e-beam) at the sample coating to cause the sample coating to emit a second set of characteristic x-rays; and
  means for measuring a first portion of the first set of characteristic x-rays and a first portion of the second set of characteristic x-rays.

44. The thin film analysis system of claim 43, wherein the means for focusing the source x-ray beam onto the sample coating comprises an x-ray reflector.

45. The thin film analysis system of claim 44, wherein the x-ray reflector comprises a doubly curved crystal.

46. The thin film analysis system of claim 44, wherein the x-ray reflector comprises a monochromator.

47. The thin film analysis system of claim 43, wherein the means for focusing the source x-ray beam onto the sample coating comprises a polycapillary array.

48. The thin film analysis system of claim 43, wherein the means for measuring comprises an energy-dispersive x-ray spectrometer.

49. The thin film analysis system of claim 43, wherein the means for measuring comprises a wavelength-dispersive x-ray spectrometer.

50. The thin film analysis system of claim 43, further comprising means for measuring a second portion of the first set of characteristic x-rays and a second portion of the second set of characteristic x-rays,
  wherein each of the first portion of the first set of characteristic x-rays has a first wavelength, wherein each of the second portion of the first set of characteristic x-rays has a second wavelength, and wherein the first wavelength is different from the second wavelength, and
  wherein each of the first portion of the second set of characteristic x-rays has a third wavelength, wherein each of the second portion of the second set of characteristic x-rays has a fourth wavelength, and wherein the third wavelength is different from the fourth wavelength.

51. A thin film analysis system for analyzing a sample coating, the thin film analysis system comprising:
  means for generating a first source x-ray beam;
  means for focusing the first source x-ray beam onto the sample coating, the first source x-ray beam being configured such that a first portion of the first source x-ray beam is reflected by the sample coating;
  means for resolving an interference pattern created by the first portion of the first source x-ray beam after being reflected by the sample coating;
  means for directing an electron beam (e-beam) at the sample coating to cause the sample coating to emit a first set of characteristic x-rays; and
  means for measuring a first portion of the first set of characteristic x-rays.

52. The thin film analysis system of claim 51, wherein the means for focusing the first source x-ray beam comprises an x-ray reflector.

53. The thin film analysis system of claim 52, wherein the x-ray reflector comprises a doubly curved crystal.

54. The thin film analysis system of claim 52, wherein the x-ray reflector comprises a monochromator.

55. The thin film analysis system of claim 52, wherein the first source x-ray beam consists of x-rays having the same wavelength, and wherein the means for focusing the first source x-ray beam comprises a polycapillary array.

56. The thin film analysis system of claim 52, wherein the means for measuring comprises an energy-dispersive x-ray spectrometer.

57. The thin film analysis system of claim 51, wherein the means for measuring comprises a wavelength-dispersive x-ray spectrometer.

58. The thin film analysis system of claim 51, further comprising means for measuring a second portion of the set of characteristic x-rays, wherein each of the first portion of the first set of characteristic x-rays has a first wavelength, wherein each of the second portion of the first set of characteristic x-rays has a second wavelength, and wherein the first wavelength is different from the second wavelength.

59. The thin film analysis system of claim 51, wherein the means for resolving the interference pattern and the means for measuring the first portion of the first set of characteristic x-rays operate at the same time.

60. The thin film analysis system of claim 51, wherein the means for resolving the interference pattern and the means for measuring the first portion of the first set of characteristic x-rays operate in rapid succession with each other.

61. The thin film analysis system of claim 51, the first source x-ray beam being further configured such that a second portion of the first source x-ray beam is absorbed by the sample coating to cause the sample coating to emit a second set of characteristic x-rays, the thin film analysis system further comprising means for measuring a first portion of the second set of characteristic x-rays.

62. The thin film analysis system of claim 61, wherein the means for focusing the first source x-ray beam comprises an x-ray reflector.

63. The thin film analysis system of claim 62, wherein the x-ray reflector comprises a doubly curved crystal.

64. The thin film analysis system of claim 62, wherein the x-ray reflector comprises a monochromator.

65. The thin film analysis system of claim 61, wherein the first source x-ray beam consists of x-rays having the same wavelength, and wherein the means for focusing the first source x-ray beam comprises a polycapillary array.

66. The thin film analysis system of claim 61, wherein the means for measuring the first portion of the first set of characteristic x-rays comprises an energy-dispersive x-ray spectrometer.

67. The thin film analysis system of claim 61, wherein the means for measuring the first portion of the first set of characteristic x-rays comprises a wavelength-dispersive x-ray spectrometer.

68. The thin film analysis system of claim 61, further comprising means for measuring a second portion of the first set of characteristic x-rays and a second portion of the second set of characteristic x-rays, wherein each of the first portion of the first set of characteristic x-rays has a first wavelength, wherein each of the second portion of the first set of characteristic x-rays has a second wavelength, and wherein the first wavelength is different from the second wavelength, and wherein each of the first portion of the second set of characteristic x-rays has a third wavelength, wherein each of the second portion of the second set of characteristic x-rays has a forth wavelength, and wherein the third wavelength is different from the fourth wavelength.

69. The thin film analysis system of claim 61, wherein the means for resolving the interference pattern and the means for measuring the first portion of the second set of characteristic x-rays operate at the same time.

70. The thin film analysis system of claim 61, wherein the means for resolving the interference pattern and the means for measuring the first portion of the second set of characteristic x-rays operate in rapid succession with each other.

\* \* \* \* \*